(12) United States Patent (10) Patent No.: US 8,308,800 B2
Chu (45) Date of Patent: Nov. 13, 2012

(54) INTRAOCULAR LENSES WITH HIGH CONTRAST HAPTICS, MATERIALS, AND METHODS

(76) Inventor: Milton W. Chu, Camarillo, CA (US)

( * ) Notice: Subject to any disclaimer, the term of this patent is extended or adjusted under 35 U.S.C. 154(b) by 194 days.

(21) Appl. No.: 12/798,777

(22) Filed: Apr. 9, 2010

(65) Prior Publication Data
US 2011/0251685 A1    Oct. 13, 2011

(51) Int. Cl.
*A61F 2/16* (2006.01)
(52) U.S. Cl. ........ 623/6.48; 623/6.5; 623/6.16; 623/6.56
(58) Field of Classification Search ............... 623/6.56, 623/6.6, 6.62, 6.48, 6.5, 6.16–6.17
See application file for complete search history.

(56) References Cited

U.S. PATENT DOCUMENTS

| | | | |
|---|---|---|---|
| 4,277,852 A * | 7/1981 | Poler | 623/6.4 |
| 4,738,680 A * | 4/1988 | Herman | 623/6.11 |
| 5,037,435 A | 8/1991 | Chang et al. | |
| 5,089,180 A | 2/1992 | Dunks et al. | |
| 5,158,719 A | 10/1992 | Chang et al. | |
| 5,182,053 A | 1/1993 | Creasman et al. | |
| 5,246,634 A * | 9/1993 | Ichikawa et al. | 264/1.7 |
| 5,252,262 A * | 10/1993 | Patel | 264/1.26 |
| 5,958,194 A | 9/1999 | Glazier | |
| 6,235,055 B1 | 5/2001 | Chu | |
| 6,447,118 B1 * | 9/2002 | Okumura et al. | 351/160 H |
| 6,637,316 B2 | 10/2003 | Engelke et al. | |
| 2008/0077238 A1* | 3/2008 | Deacon et al. | 623/6.16 |
| 2010/0094414 A1* | 4/2010 | Downer et al. | 623/6.27 |

FOREIGN PATENT DOCUMENTS

WO   WO 2011127079 A1 *  10/2011

* cited by examiner

*Primary Examiner* — Paul Prebilic
(74) *Attorney, Agent, or Firm* — Foley & Lardner LLP

(57) ABSTRACT

Intraocular lenses with high contrast haptics, materials and methods for making optical blanks and lenses, and methods of use are disclosed and claimed. Such lenses may provide easily recognizable visual cues that may be used to detect and correct misorientation of lenses prior to and during use.

14 Claims, 8 Drawing Sheets

INTRAOCULAR LENSES WITH HIGH CONTRAST HAPTICS, MATERIALS, AND METHODS

BACKGROUND

This disclosure relates to improved intraocular lenses for implantation in the eye and improved methods of anterior-posterior orientation. Embodiments of the improved intraocular lenses have at least one haptic support member that exhibits an improved visual guide to anterior-posterior orientation through use of improved coloration, patterning, or texturing.

Intraocular lenses (IOLs) are positioned in the anterior chamber, at the iris plane, in the ciliary suclus space, in the posterior chamber, in the capsular bag or other intended spaces inside the eye. Such lenses may be used in a variety of surgical procedures which include, but are not limited to, cataract surgery, clear lensectomy/vision correction, secondary implantation of an intraocular lens, phakic intraocular lens, and other vision correcting procedures.

It is preferable that intraocular lenses be implanted with the correct anterior-posterior orientation in order for the lens optics to achieve the desired optical result and so that the intraocular lens will have the correct position and desired movement, if so designed, inside the eye. Many modern intraocular lenses have advanced optical qualities, such as asymmetrical anterior and posterior optics, which may require proper orientation inside the eye in order to achieve the desired and intended visual results.

Many intraocular lenses also exhibit unique geometry of the haptic in relation to the optic, commonly known as haptic angulation, which may employ a preferred anterior-posterior orientation of the intraocular lens to achieve not only the desired visual result but also to discourage unwanted and potentially harmful interaction of the intraocular lens with ocular tissue, such as the cornea, iris, ciliary body, and lens capsule.

In some cases, an interaction with ocular tissue may be desired, such as the case when positive angulation of the haptics is used to position the IOL against the posterior capsule to attempt to prevent the inward growth of epithelial cells that may lead to a secondary cataract. If such an intraocular lens is implanted in the reverse orientation, upside down, this design intention may not be realized. In such a case, there is the potential for unwanted and potentially harmful interactions between the intraocular lens and iris or ciliary body.

There are also a growing number of intraocular lenses which are designed to move inside the eye, which may provide additional optical benefits such as accommodation and enhanced voluntary focusing of vision. These intraocular lenses frequently feature haptics with more complex shapes and angulations in order to attempt to produce desired movement of the lens optic. If these intraocular lens are positioned incorrectly, the resulting movement of the intraocular lens may be abnormal or reversed and may create optical problems and possible tissue interaction problems.

Currently, intraocular lens manufacturers address the issue of intraocular lens orientation by using design features, such as holes, notches, and tabs, to signal the proper orientation of the intraocular lens. However, these design features may be difficult to see and use for several reasons.

First, the design features used to identify the orientation of the intraocular lens, by their very nature, may be very small and difficult to see. Next, the intraocular lens is typically made out of a highly transparent and colorless material, making these subtle features even more difficult to discern. When the lens is folded and rolled-up in the injector, these design features cannot be identified or used to determine whether the intraocular lens is oriented correctly. When the lens is unfolded in an eye with a small pupil, it is frequently difficult or impossible to see the orientation notch, hole or tab, which may be hidden behind the iris. Furthermore, these design orientation features vary from lens model to lens model, increasing the potential for confusion.

When the intraocular lens is oriented incorrectly, the intraocular lens may unfold upside down inside the eye. In such a case, the orientation may be corrected, for example, by inserting micro-scissors inside the eye, cutting the intraocular lens into pieces, and then extracting the lens pieces. Surgical trauma may occur in the form of iris tears, intraocular bleeding, endothelial corneal damage, and rupture of lens capsule and/or zonules.

In the U.S., haptics may presently be colored using one or more of the three pigments that the FDA has approved for use: copper phthalocyanine, D&C (Drug and Cosmetic) Green No. 6 (IUPAC name: 1,4-bis(4-methylanilino)antracene-9,10-dione), and D&C Violet No. 2 (1-hydroxy-4-[(4-methylphenyl)amino]-9,10-anthracenedione). However, creating a strong and high contrast color difference using these pigments can be difficult. Copper phthalocyanine and D&C green No. 6 both have similar blue colors, while D&C Violet No. 2 has a violet color that does not strikingly contrast with the other two blue colors. Because haptics are typically transparent and thin, the difficulty in recognizing the differences among these colors is exacerbated when these colorants are used in haptics.

SUMMARY

Some embodiments provide an intraocular lens comprising a central lens optic and at least one haptic projected outwardly from the optic, where the haptic has an anterior side and a posterior side of contrasting colors, patterns, or textures, and where the haptic comprises at least one first layer comprising greater than 1 wt % titanium dioxide or at least about 2 wt % titanium dioxide. The first layer may be opaque. The first layer may comprise one or more colorants, including, but not limited to copper phthalocyanine, D&C Violet No. 2, or D&C Green No. 6. In some cases, the first layer may comprise at least one polymer or copolymer comprising an imide linkage, such as at least one polyimide or copolyimide.

In some embodiments, the intraocular lens will further comprise at least one second layer, where the colors, patterns, or textures of the first and second layers are contrasting. The second layer may comprise one or more colorants, including, but not limited to, copper phthalocyanine, D&C Violet No. 2, or D&C Green No. 6. In some cases, the second layer may comprise at least one polymer or copolymer comprising an imide linkage, such as polyimides or copolyimides. The second layer may comprise carbon black. Some lenses may comprise haptics that are positively angulated, negatively angulated, or angulated in a complex fashion.

Other embodiments provide methods for using an intraocular lens. Such methods comprise detecting one or more colors, patterns, or textures from at least a portion of the intraocular lens, identifying the lens' orientation from the one or more colors, patterns, or textures, and correcting the lens' orientation, if it is different from a predetermined orientation.

Still other embodiments provide a disc from which an intraocular lens may be fabricated, where the disc comprises a transparent optic and an annulus, where the annulus surrounds the optic and contacts it, where the annulus comprises two or more surfaces with contrasting colors, patterns, or textures, and where the annulus comprises a layer comprising greater than 1 wt % titanium dioxide or at least about 2 wt % titanium dioxide.

Yet other embodiments provide methods for making a disc from which these intraocular lenses may be fabricated. Some methods comprise providing an object and polymerizing at least one first monomer to form a first region that contacts the object. In some cases, the methods further comprise polymerizing at least one second monomer to form a second region, where the second monomer may be the same as or different from the first monomer, where the second region contacts the first region or the object or both, where the first and second regions have contrasting colors, patterns, or textures, and where one of the regions comprises greater than 1 wt % titanium dioxide or at least about 2 wt % titanium dioxide. In some cases, the first region or the second region may be annular in shape, or both regions may be annular in shape.

Yet still other embodiments provide methods for making an intraocular lens. Such methods comprise providing a central lens optic; forming at least one haptic having an anterior side and a posterior side, including forming at least one layer comprising greater than 1 wt % titanium dioxide or at least about 2 wt % titanium dioxide to provide one of the anterior and posterior sides with at least one first color, pattern, or texture that contrasts with at least one second color, pattern, or texture of the other of the anterior or posterior sides; and projecting the at least one haptic outwardly from the central lens optic.

These and other embodiments will be understood by those skilled in the art, based on the disclosure, examples, and claims herein.

BRIEF DESCRIPTION OF FIGURES

The patent or application file contains at least one drawing executed in color. Copies of this patent or patent application with color drawing(s) will be provided by the Office upon request and payment of the necessary fee.

DETAILED DESCRIPTION

Devices

Figure 1A:
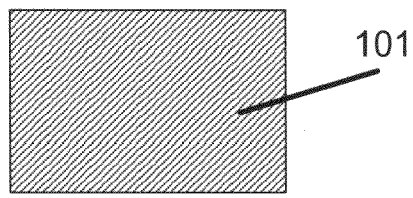
FIG. 1A depicts a colored (co-)polymer disc that has been cut from a section of a colored (co-)polymer rod, viewed as a cross-section of the disc.

Haptics with distinguishable anterior and posterior sides are described in U.S. Pat. No. 6,235,055 to Chu, filed Aug. 9, 1999, which is incorporated by reference in its entirety. Embodiments of the invention provide haptics for intraocular lenses having an improved multiply colored, multiply patterned, or multiply textured appearance, where the anterior and posterior sides are more easily distinguishable. Such haptics may provide an improved and superior method by which to confirm the anterior-posterior orientation of the intraocular lens.

The improved multiply colored, multiply patterned, or multiply textured haptics may be detected by, for example, viewing, when the lens is folded and rolled within the lens inserter, providing a way to determine if the lens is properly oriented before it has been injected and unfolded inside the eye.

Furthermore, when the lens is only partially introduced into the eye, such as when only the leading haptics have emerged inside the eye while most of the lens optic and the trailing haptics are still folded inside the inserter, the improved multiply colored, multiply patterned, or multiply textured sides of the leading haptics may be used to determine if the lens has the correct orientation, which may help to prevent the intraocular lens from unfolding upside down.

Once unfolded in the eye, the intensely contrasting anterior and posterior sides of the haptic may provide a method to determine the lens orientation, especially under the difficult conditions of a small pupil, where frequently only a small portion of the haptic may be able to be viewed. With a conventional haptic, a small pupil may make it extremely difficult or impossible to see an orientation notch, hole, or tab, making more difficult the determination of correct anterior-posterior orientation.

The anterior and posterior surfaces of the haptics may be made more visually distinct by the addition to the polymer or copolymer ("(co-)polymer") of sub-micron sized titanium dioxide at a concentration by weight greater than 1 wt %, or at least about 2 wt %, up to about 15 wt % or more in order to create enough opacity to hide the colors, patterns, or textures of the opposite side. An average titanium dioxide particle size of about 0.25 microns may be used in preferred embodiments. The sub-micron titanium dioxide may preferably be dispersed in one or more of the monomers or comonomers ("(co-)monomers") or uncured (co-)polymers that will be used to form the haptics. When titanium dioxide is added to clear (co-)polymer, the titanium dioxide may impart a white opaque appearance. When titanium dioxide is added to (co-)polyimides that are naturally translucent amber in color, the titanium dioxide may give the (co-)polyimide an opaque yellow color.

Enough titanium dioxide may be added to also create a level of opacity that will "hide" the colors, patterns, or textures of the opposite or posterior side. The amount of titanium dioxide needed to create this sufficient level of opacity and hide is roughly inversely related to the thickness of the haptic. A relatively thin haptic, for example 1-2 mils in thickness, may employ as much as 8-15 wt % titanium dioxide, while a thicker haptic of 10 mils may employ greater than 1-8 wt % titanium dioxide.

In some cases, enough titanium dioxide may be added to create a level of opacity sufficient to reduce transmission of 500 nm light from the anterior side through the haptic to the posterior side, or from the posterior side through the haptic to the anterior side, by 50% relative an identical haptic that has no titanium dioxide. Such a measurement may be made with the haptics immersed in a clear liquid, such as water, saline, or the liquid aqueous humor of the eye.

In preferred embodiments, the titanium dioxide is dispersed in (co-)monomers or uncured (co-)polymers. Such dispersions may also optionally include colorant particles. Conventional mixing techniques may be employed to prepare dispersions, including, but not limited to, closed-rotor, ultrasound, rotor-stator, colloid mill, and homogenizers. Such methods may, however, exhibit limited effectiveness when dealing with dense particles, such as titanium dioxide.

Alternatively, a microfluidizer processor, such as those produced by Microfluidics Corp in Newton, Mass., may be used to produce high shear, for example, shear rates above 10,000,000 $sec^{-1}$, often allowing relatively fine and substantially homogenous dispersions of titanium dioxide particles and colorant particles to be formed. The microfluidizer dispersions may typically exhibit long shelf-lives before sedimentation occurs. These dispersions may often be reconstituted quickly with gentle agitation. Moreover, such microfluidizer dispersion processes may often be readily scaled to larger volumes.

Matching the type of titanium dioxide to the particular polymer application may also improve homogeneity and other qualities of the dispersion. For example, titanium dioxide particles with a surface treatment of alumina may exhibit superior dispersive characteristics in terms of good initial wetting, ease of breaking aggregates and agglomerates, and exhibiting less propensity for flocculation when used with liquid acrylic monomers.

Coloration other than opaque white or opaque yellow (for (co-)polyimides) may be achieved using colorant or pigments, including, but not limited to, one or more of the three pigments the FDA has approved for use in intraocular lens haptics: copper phthalocyanine, D&C green No. 6, and D&C violet No. 2. Other suitable colorants or pigments may also be employed, either as an alternative to the FDA approved pigments, or in various combinations with one or more of them, as allowed by appropriate laws or regulations in the U.S. or in other countries. In some cases, titanium dioxide may be used with the chosen colorants or to enable or increase opacity, which in turn may increase the level of "hide" of the colors, patterns, or textures of the opposite side of the haptic.

In some embodiments, multiple patterns may be used in or on haptics, such as two, three, or more patterns. Such patterns may include, but are not limited to, one or more of dots, line segments, arcs, squares, cross-hatching, ovals, circles, polygons with three or more sides, and so on. Some patterns may reside within other patterns. Some patterns may overlap with other patterns. Patterns may be formed using one or more materials.

In some embodiments, multiple textures may be used in or on haptics, such as two, three, or more textures. Such textures may include, but are not limited to, smooth, hard, soft, bristled, rubbery, fuzzy, wavy, bumpy, and the like. Textures may be formed using one or more materials.

In some embodiments, multiple colors, multiple patterns, or multiple textures may be used in or on haptics, including, but not limited, two or more colors, two or more patterns, or two or more textures. In some cases, two or more colors may be used with two or more patterns, or two or more colors may be used with two or more textures, or two or more patterns may be used with two or more textures. In some cases, two or more colors may be used with two or more patterns and two or more textures.

Methods of Fabrication

A method according to an embodiment of the inventions is provided to create a single-piece intraocular lens using a multiply colored, multiply patterned, or multiply textured blank disc which may comprise a clear central optic surrounded by one or more colored, patterned, or textured annular rings. For example, this multiply colored, multiply patterned, or multiply textured lens blank disc may then be modified by using any suitable technique, including, but not limited to, micro-lathe manufacturing techniques, to produce a wide variety of intraocular lenses that feature a transparent, preferably clear, central optic with at least one or more haptics protruding from the optic bearing an appearance on the anterior and posterior surfaces that is multiply colored, multiply patterned, or multiply textured.

Various processes may be used to create a multiply colored, multiply patterned, or multiply textured blank disc. For example, the starting point may be forming a ring space around the optic of a clear blank disc, according to any suitable process, for example, by milling. The ring space may be filled with one or more colored (co-)monomers or uncured (co-)polymers, which are polymerized. Then a more shallow opening may be created in this filled ring area, according to any suitable process, including, but not limited to, milling. This opening may be filled with additional possibly differently colored (co-)monomers or uncured (co-)polymers, which are then polymerized. In some embodiments, multiple patterns or textures may be added to one or more surfaces of the disc using any suitable method, including, but not limited to, stamping, drawing, printing, engraving, scribing, and the like.

Alternatively, colored opaque monomers (co-)monomers or uncured (co-)polymers may be poured into a cylindrical mold and polymerized. An optic hole space may be formed at the center of the cured colored rod, according to any suitable process, for example, by milling. The optic hole space may be filled with clear (co-)monomers or uncured (co-)polymers and polymerized. Blank discs are formed from the rod by, for example, cutting. A ring space around the optic may be formed, according to any suitable process, including, but not limited to, milling, with a depth approximately equal to the mid-point of the intended IOL haptic. The ring space may be filled with possibly different colored (co-)monomers or uncured (co-)polymers and polymerized. In some embodiments, multiple patterns or textures may be added to one or more surfaces of the disc using any suitable method, including, but not limited to, stamping, drawing, printing, engraving, and the like.

Another approach is to apply a coating to the either or both of the anterior and posterior sides of the haptic of a formed IOL by a suitable process, including, but not limited to, painting or coating. An uncured liquid dispersion of (co-)monomers or uncured (co-)polymers, along with pigments, cross-linkers, and initiators, may, for example, be sprayed on the haptic surfaces using micro-coating techniques and/or inkjet micro spray techniques and then polymerized with UV curing. In some embodiments, multiple patterns or textures may be added to one or more surfaces of the disc using any suitable method, including, but not limited to, stamping, drawing, printing, engraving, scribing, and the like.

In some embodiments, ultraviolet (UV) laser cutting may be used as an alternative to such methods as milling or etching. UV laser cutting of haptics may provide several benefits. First laser cutting may produce "drop-out" pieces without requiring the additional processes of hand de-tabbing and trimming. Second, laser cutting may produce more intricate and finely detailed haptics than other processes that are constrained by thickness and geometry. Third, laser cutting may provide an advantaged part yield compared to some other processes. Finally, laser cutting may allow for rapid-prototyping at a low cost and fast turn around time.

In some embodiments, haptics and optics may be separately fabricated. The haptics may be preferably attached to an optic's peripheral edge in a manner that minimizes interference with operation of the optic. For example, one or more bores may be provided in the lens optic by any suitable method, including, but not limited to, drilling or molding. The end of one or more haptics may be permanently or removably secured by any suitable method, including, but not limited to, laser staking, gluing, and molding the optic about the haptics.

Alternatively, the haptics and lens optic may be formed as a one-piece construction. In such a case, a blank disc may comprise a central transparent, preferably clear, portion destined to become the lens optic and one or more non-central portions destined to become one or more haptics. Such discs may be transformed into optics and haptics by any suitable method, including, but not limited to, cutting, etching, milling, machining, and the like, to obtain the optics and haptics of the desired dimensions.

Further embodiments relate to methods for creating high contrast multiply colored, multiply patterned, or multiply textured haptics for multi-piece intraocular lenses. For example, a thin film (1-2 mils) of polyimide may be made opaque yellow with the addition of titanium dioxide. "(Co-)polyimide" may be understood to mean any polymer or copolymer having one or more repeat units bearing an imide linkage. The resulting color may be opaque yellow due to the (co-)polyimide's typical amber color. Next a second thin film (1 mil) of a (co-)polyimide without titanium dioxide modification may be bonded to the (co-)polyimide/titanium dioxide film, for example, by using high heat and pressure and/or adhesives such as polytetrafluoroethylene (PTFE), to form a laminate. Additional films of (co-)polyimide may optionally be used in the laminate, for example, to achieve a required thickness. The color of the plain (co-)polyimide may appear dark amber against the opaque yellow (co-)polyimide/titanium dioxide film. In some embodiments, multiple patterns or textures may be added to one or more surfaces of the laminate using any suitable method, including, but not limited to, stamping, drawing, printing, engraving, scribing, and the like.

(Co-)polyimide films may also be made opaque black with carbon black. Carbon black may be successfully dispersed in (co-)polyimide and in concentrations on the order of 5-30%, for example, in order to produce a black opaque color. These black films may be bonded as a layer of the laminate to create an even greater color contrast with the opposite opaque yellow side.

Such laminates may be used to prepare haptics. For example, various processes, including, but not limited to, UV laser cutting may be used to produce haptics from laminates comprising titanium dioxide and carbon black. In some embodiments, multiple patterns or textures may be added to one or more surfaces of the haptics using any suitable method, including, but not limited to, stamping, drawing, printing, engraving, scribing, and the like.

Some embodiments further provide methods to create single-piece intraocular lenses using a multiply colored, multiply patterned, or multiply textured blank disc where two or more colored, patterned, or textured rings surround the clear optic center. Such a blank disc may be used to create single-piece intraocular lenses with positive or negative haptic angulation, or with other even more complex designs. Such a haptic with positive angulation, negative angulation, or more complex angulation, is said to be "angulated."

For example, the anterior surface of a bottom ring and the posterior surface of an upper ring may be created to have the unique geometric shapes or angulation of the finished haptic. Since the multiply colored, multiply patterned, or multiply textured double annular rings may be created sequentially, once the bottom ring has been polymerized it may be shaped by any suitable method, for example, but not limited to, micro-machining, with accuracy to create a desired geometrical shape for the upper ring. The liquid (co-)monomers or uncured (co-)polymers, when poured into the upper ring space, will automatically assume the angulation shape defined by the bottom ring.

In the case of creating intraocular lenses with positive angulation, where the haptics are angled anteriorly relative to the optic in the "z" axis, the interface of the bottom and top ring may be shaped and sequentially polymerized to have this same angulation shape. In this way the blank disc may produce an intraocular lens with haptic angulation, where the anterior and posterior sides have two different colors, patterns, or textures.

In the case of creating intraocular lenses with negative haptic angulation, where the haptics are angled posteriorly relative to the optic in the "z" axis, the interface of the bottom and top ring may be shaped and sequentially polymerized to have the same angulation shape. In this way the blank disc may produce an intraocular lens with haptic angulation, where the anterior and posterior sides have two or more different colors, patterns, or textures.

In a similar way, the unique multiply colored, multiply patterned, or multiply textured appearance may also follow along the anterior and posterior sides of haptics having even more complex geometrical shapes than simple angulation.

The polymers or copolymers used to create the haptics may be obtained by polymerization of a single monomer, such as methyl methacrylate (MMA) or by copolymerization of various hydrophilic or hydrophobic comonomers, such as 2-hydroxyethyl methacrylate (HEMA), in various combinations thereof. A copolymer with HEMA and MMA repeat units may be referred to as pHEMA-MMA.

The exact composition may vary according to the desired physical characteristics of the haptics. If the haptics are desired to have the same characteristics as the optic, then for example a pHEMA-MMA copolymer with HEMA to MMA ratio of 80:20 might be used. If the haptics are desired to be more firm, then the ratio might be changed to one with a higher fraction of MMA.

Any (co-)monomer or uncured copolymer that is suitable for use in preparing haptics may be used, including, but not limited to, those used in producing hydrophilic, hydrophobic, and silicone-based haptics. Examples of hydrophilic (co-)monomers include, but are not limited to, 2-hydroxyethylacrylate, 2-hydroxyethylmethacrylate, ethoxyethylmethacrylate, and acrylamide. Examples of hydrophobic (co-)monomers include, but are not limited to, glyceralmethacrylate, diacetoneacrylamide, lauryl methacrylate, butyl methacrylate, 2-ethylhexylmethacrylate, vinyl hydroxyacetate, vinyl hydroxyproprionate, vinyl hydroxybutyrate, and N-vinyl lactams. Other examples of (co-)monomers and uncured (co-)polymers include, but are not limited to, N,N-dimethylacrylamide, methacrylic acid, N-vinyl pyyolidone, tris-(trimethylsiloxysilyl)propylvinyl carbonate, N-carboxyvinyl ester, poly[dimethyldoloxy]di[silylbutanol]bis[vinyl carbamate], polyvinyl pyrrolidone, polydimethylsiloxane, and fluoroether macromers. Polymerization may be started using thermal initiators, such as azobisisobutyronitrile (AIBN), benzoyl peroxide, potassium persulfate, ammonium persulfate, benzophenone, methacryloyloxy benzophenone and N,N-dimethylaminoethyl methacrylate, and the like, used either as sole agents or in various combinations thereof.

Photoinitiators may also be employed on thin films and when faster polymerization times are sought. These agents include, but are not limited to, anthraquinones, methylanthraquinones, camphoquinone tertiary amine hybrid, benzoin ethyl ether, and the like. Examples of photoinitiators also include, but are not limited to, 1-[4-(2-hydroxyethyoxy)-phenyl]-2-hydroxy-2-methyl-1-propane-1-one (IRGACURE 2959), phenyl-bis(2,4,6-trimethylbenzoylphosphine oxide) (IRGACURE 819), and the like.

The (co-)polymers may be subjected to inter-molecular crosslinking, to adjust their physical strength and water content. Crosslinking agents may include, but are not limited to, acrylate or acrylamide-based compounds, for example, ethylene glycol dimethacrylate (EGDMA), diethylene glycol bismethacrylate, or N,N-methylene bis(acrylamide), and the like. The amount of the crosslinking agent used may be the range of 0.01-2.0 wt % based on the total weight of the monomers, and may be preferably in the range of 0.05-1.5 wt %.

Although various polymerization techniques may be employed, ultraviolet (UV) curing with high energy UV sources, such as, but not limited to, medium pressure mercury lamps, may provide cure times of, for example, a few seconds to a few minutes. Such rapid polymerization may reduce sedimentation of titanium dioxide and pigment particles due to the decreased time during which the polymerization medium is at low viscosities.

Since pigmented dispersions may compete with the photoinitiator to absorb specific wavelengths of light, it may be preferable to select a photoinitiator that may be excited by light at a wavelength that is able to penetrate the pigmented dispersion. Such a selection may allow improved spatial homogeneity of curing, sometimes referred to as "through cure."

Undesired surface morphologies, such as ripples or bubbles, may be reduced or eliminated by curing the substrate in an oxygen deprived environment. Such an oxygen deprived environment may be provided by any suitable method, including, but not limited to, use of $CO_2$ gas blanketing or purging. Surface curing may also be reduced by such methods as, for example, simultaneously filtering both UVC and UVB wavelengths of ultraviolet light with optical filters placed between the UV lamp and the substrate.

Embodiments of FIGS. 1-5

Figure 1B:
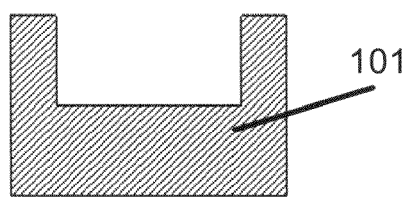
FIG. 1B depicts the disc of FIG. 1A, where a depression has been formed in a portion of one surface.
Figure 1C:
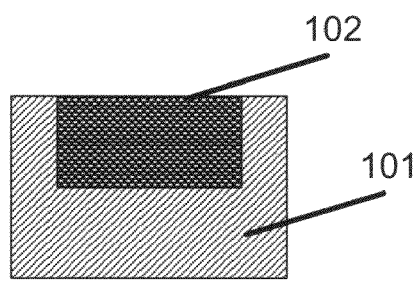
FIG. 1C depicts the disc of FIG. 1B, where the depression has been filled with uncured (co-)monomers, at least one colorant, and titanium dioxide, then polymerized to form an opaque colored (co-)polymer that has a color, pattern, or texture different from that of the colored disc.
Figure 1D:
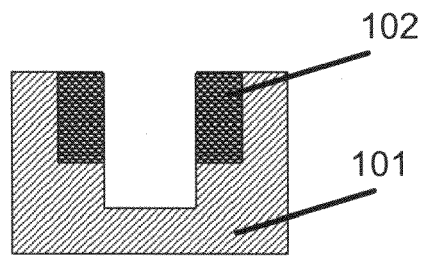
FIG. 1D depicts the disc of FIG. 1C, where an optical zone has been formed in portions of the (co-)polymer and the underlying colored disc.
Figure 1E:
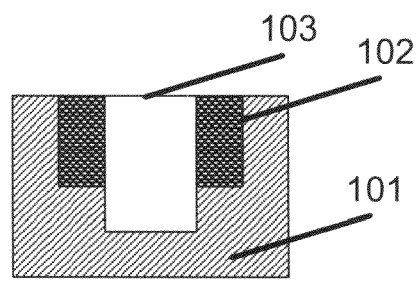
FIG. 1E depicts the disc of FIG. 1D, where the optical zone has been filled with uncured (co-)monomers, then polymerized to form a clear (co-)polymer.

FIG. 1A depicts a cross-sectional view of a transparent (co-)polymer disc (101) that is cut from a section of a colored (co-)polymer rod. As shown in FIG. 1B, a depression is introduced into a surface of disc (101) by any suitable means, including, but not limited to, milling. In FIG. 1C, the depression is filled with (co-)monomers or uncured (co-)polymers, at least one colorant, titanium dioxide, and optionally initiators, crosslinkers, and the like, which are polymerized to form an opaque colored (co-)polymer (102) that has a color different than disc (101). An optical zone is then formed in portions of the (co-)polymer (102) and the underlying disc (101). The zone is formed using any suitable process, including, but not limited to, milling, as shown in FIG. 1D. This zone is then filled with (co-)monomers or uncured (co-)polymers, and optionally initiators, crosslinkers, and the like, which are polymerized to form a clear (co-)polymer (103), as shown in FIG. 1E. The resulting disc has a distinguishable appearance, depending upon whether it is viewed from above or below. Note that the (co-)polymers of (101), (102), and (103) need not have identical compositions or molecular weights.

Figure 2A:
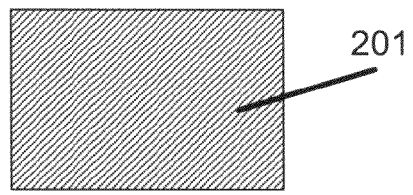
FIG. 2A depicts a clear (co-)polymer disc, viewed as a cross-section of the disc.
Figure 2B:
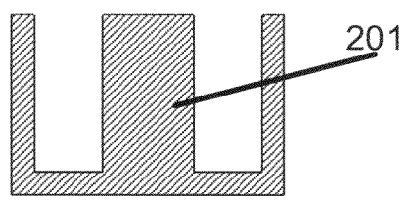
FIG. 2B depicts the disc of FIG. 2A, where an annular depression has been formed in a portion of one surface.
Figure 2C:
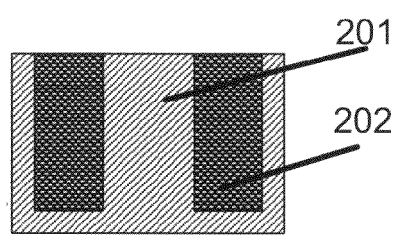
FIG. 2C depicts the disc of FIG. 2B, where the annular depression has been filled with uncured (co-)monomers and at least one first colorant, then polymerized to form a first colored (co-)polymer annulus.
Figure 2D:
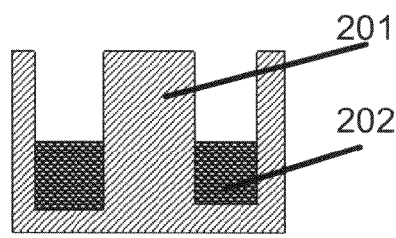
FIG. 2D depicts the disc of FIG. 2C, where an annular depression has been formed in a portion of the colored (co-)polymer annulus.
Figure 2E:
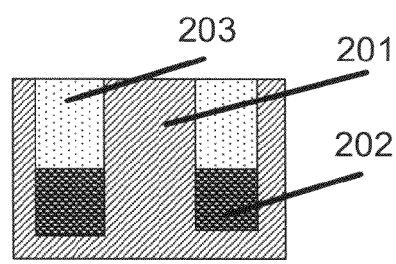
FIG. 2E depicts the disc of FIG. 2D, where the annular depression has been filled with uncured (co-)monomers, titanium dioxide, and at least one second colorant, then polymerized to form an second opaque colored (co-)polymer annulus.

FIG. 2A depicts a cross-sectional view of a clear (co-)polymer disc (201) that is cut from a section of a clear (co-)polymer rod. As shown in FIG. 2B, an annular depression is introduced into a surface of disc (201) by any suitable means, including, but not limited to, milling. In FIG. 2C, the depression is filled with (co-)monomers or uncured (co-)polymers, at least one first colorant, and optionally initiators, crosslinkers, and the like, which are polymerized to form a colored (co-)polymer annulus (202). A portion of the colored (co-)polymer annulus is then removed to form another annular depression, as shown in FIG. 2D. Such removing may be performed by any suitable process, including, but not limited to, milling. This annular depression is then filled with (co-)monomers or uncured (co-)polymers, at least one second colorant, titanium dioxide, and optionally initiators, crosslinkers, and the like, which are polymerized to form an opaque colored (co-)polymer annulus (203) that has a color different from the colored disc (201), as shown in FIG. 2E. The resulting disc has a distinguishable appearance, depending upon whether it is viewed from above or below. Note that the (co-)polymers of (201), (202), and (203) need not have identical compositions or molecular weights.

Figure 3A:
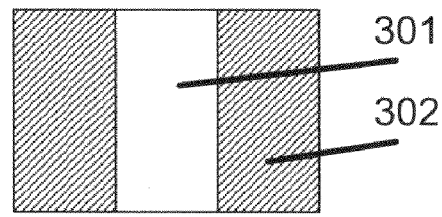
FIG. 3A depicts a cross-sectional view of a (co-)polymer disc that has been cut from a section of a clear (co-)polymer rod that had been coated with uncured (co-)monomers, at least one first colorant, and titanium dioxide, then polymerized to form a first opaque colored (co-)polymer annulus.
Figure 3B:
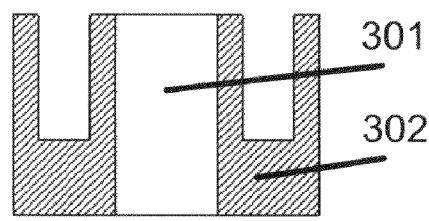
FIG. 3B depicts the disc of FIG. 3A, where an annular depression has been formed in a portion of the colored annulus.
Figure 3C:
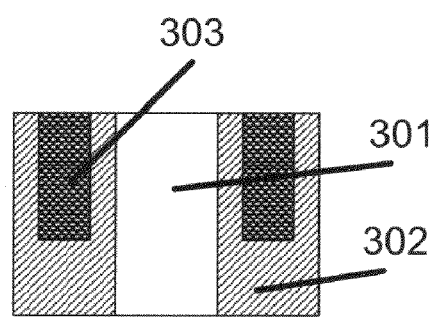
FIG. 3C depicts the milled disc of FIG. 3B, where the annular depression has been filled with (co-)monomers and at least one second colorant, then polymerized to form a second colored (co-)polymer annulus.

FIG. 3A depicts a cross-sectional view a disc with a clear (co-)polymer core (301) surrounded by an opaque colored (co-)polymer annulus (302). Such a disc might be fabricated by coating a clear (co-)polymer rod with (co-)monomers or uncured (co-)polymers, at least one first colorant, titanium dioxide, and optionally initiators, crosslinkers, and the like, which may be polymerized to form an annular coating on the rod. The coated rod may be sectioned to form the disc of FIG. 3A. As shown in FIG. 3B, an annular depression is introduced into the opaque annulus (302) by any suitable means, including, but not limited to, milling. The annular depression is then filled with (co-)monomers or uncured (co-)polymers, at least one second colorant, and optionally initiators, crosslinkers, and the like, which are polymerized to form a colored (co-)polymer annulus (303) that has a different color from the colored annulus (302), as shown in FIG. 3C. The resulting disc has a distinguishable appearance, depending upon whether it is viewed from above or below. Note that the (co-)polymers of (301), (302), and (303) need not have identical compositions or molecular weights.

Figure 4A:
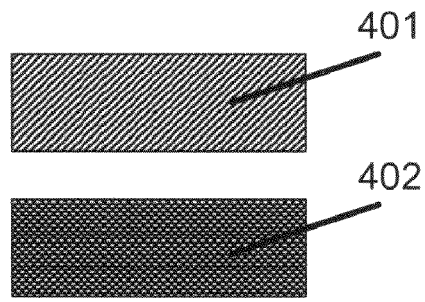
FIG. 4A depicts cross-sectional views of two (co-)polymer discs, one containing titanium dioxide and at least one first colorant, the other containing at least one second colorant.
Figure 4B:
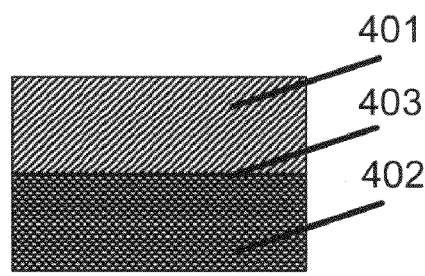
FIG. 4B depicts the discs of FIG. 4A that have been bonded together.
Figure 4C:
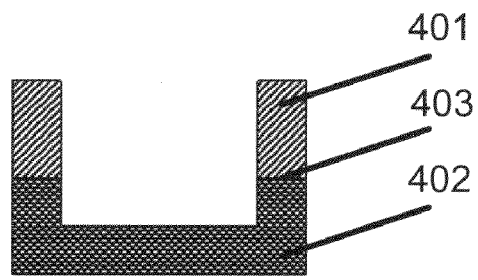
FIG. 4C depicts the bonded discs of FIG. 4B that have been milled to form an optical zone.
Figure 4D:
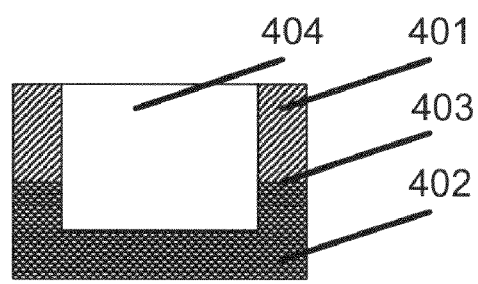
FIG. 4D depicts the bonded discs of FIG. 4C, where the optical zone has been filled with (co-)monomers, then polymerized to form a clear (co-)polymer.

FIG. 4A depicts cross-sectional views of discs (401) and (402) that have contrasting colors. For example, disc (401) may comprise cured copolymer comprising titanium dioxide and optionally comprising colorants, crosslinkers, initiators, and the like, and disc (402) may comprise cured copolymer comprising at least one colorant and optionally titanium dioxide, crosslinkers, initiators, and the like, so that the colors of the two discs are contrasting. As shown in FIG. 4B, discs (401) and (402) are bonded together using any suitable method, including, but not limited to, adhesion, heat, pressure, ultraviolet radiation, and sonification. Depending on how the discs are bonded, the interface (403) between the discs may consist of the discs alone or may comprise additional compounds, such as adhesives. An optical zone is then formed in the bonded discs using any suitable method, including, but not limited to, milling, as shown in FIG. 4C. The depression is then filled with (co-)monomers or uncured (co-)polymers, and optionally initiators, crosslinkers, and the like, which are polymerized to form a clear (co-)polymer (404), as shown in FIG. 4D. The resulting blank disc has a distinguishable appearance, depending upon whether it is viewed from above or below. Note that the discs (401) and (402) need not have identical compositions or molecular weights.

Figure 5A:
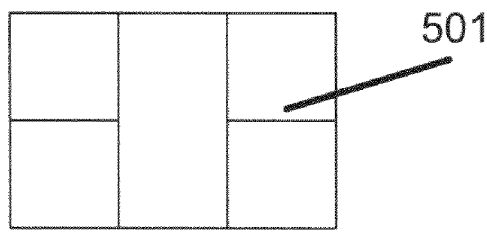
FIG. 5A depicts a cross-sectional view of flat haptic rings with no angulation

FIG. 5A depicts a cross-sectional view of a disc, where the two haptic rings have no angulation. The anterior surface (501) of the bottom ring has not been modified to create a modified geometrical shape for the upper ring.

Figure 5B:
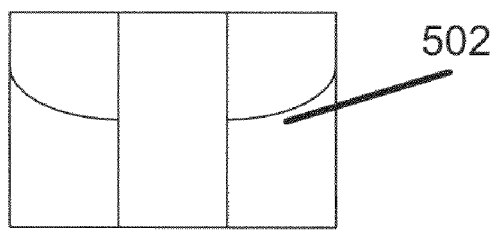
FIG. 5B depicts a cross-sectional view of curved haptic rings with positive angulation.

FIG. 5B depicts a cross-sectional view of a disc where the two haptics are angled anteriorly relative to the optic. The anterior surface (502) of the bottom ring has been modified by suitable methods, including, but not limited to, machining, to create a modified geometrical shape for the upper ring, so that the intraocular lens will have positive angulation.

Figure 5C:
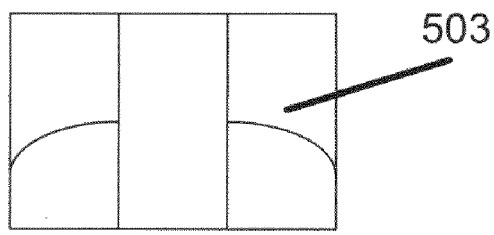
FIG. 5C depicts a cross-sectional view of curved haptic rings with negative angulation.

FIG. 5C depicts a cross-sectional view of a disc where the two haptics are angled posteriorly relative to the optic. The anterior surface (503) of the bottom ring has been modified by suitable methods, including, but not limited to, machining, to create a modified geometrical shape for the upper ring, so that the intraocular lens will have negative angulation.

Figure 5D:
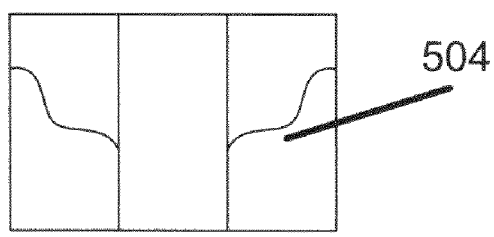
FIG. 5D depicts a cross-sectional view of complex shaped haptic rings.

FIG. 5D depicts a cross-sectional view of a disc where the two haptics are angled in a complex fashion relative to the optic. The anterior surface (504) of the bottom ring has been modified by suitable methods, including, but not limited to, machining, to create a modified geometrical shape for the upper ring, so that the intraocular lens haptic will have an advanced design and the intraocular lens will have complex angulation.

Figure 6A:
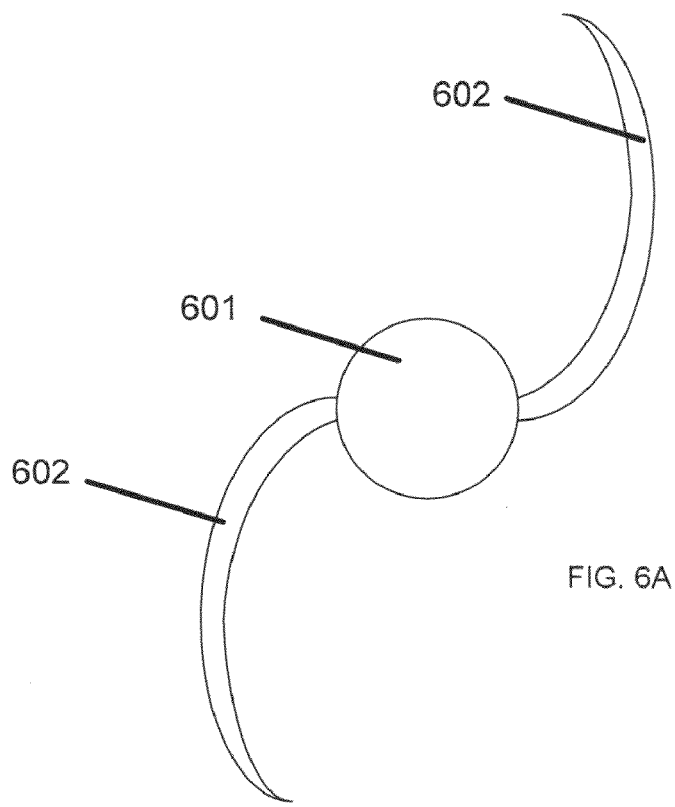
FIG. 6A depicts an anterior view of an intraocular lens.
Figure 6B:
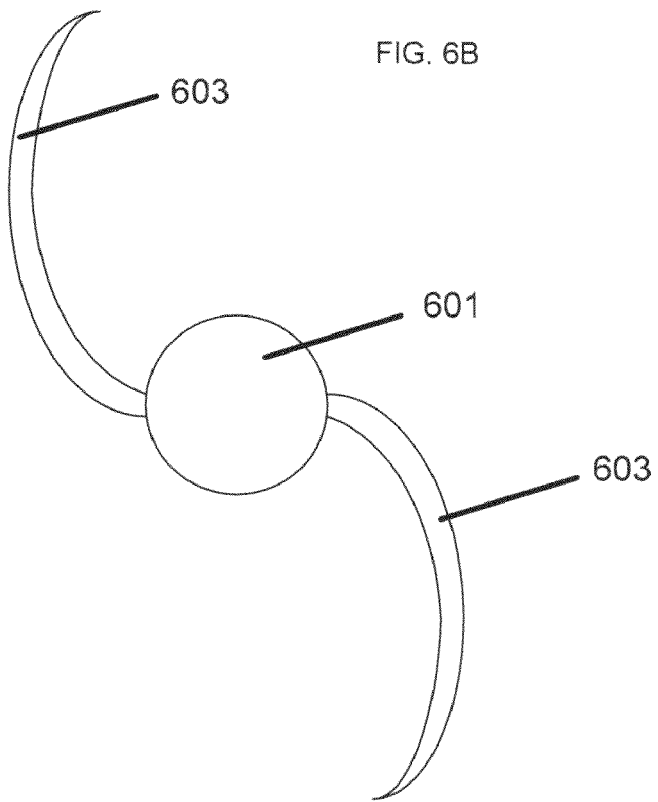
FIG. 6B depicts a posterior view of an intraocular lens.

FIG. 6A depicts an anterior view of an intraocular lens comprising a central optic (601) and one or more haptics that have one or more anterior surfaces (602). The optic and haptics may be formed from a single blank disc or they may be formed from separate materials and joined together. Any suitable fabrication methods may be used, including, but not limited to, milling, laser cutting, laser staking, gluing, and molding. For example, U.S. Pat. No. 6,235,055 to Chu, filed Aug. 9, 1999 and incorporated by reference in its entirety, describes construction of an intraocular lens from separate optics and haptics. FIG. 6B depicts a posterior view of the intraocular lens of FIG. 6A, where the one or more haptics have one or more posterior surfaces. Surfaces (602) and (603) may comprise colored, patterned, or textured layers that contrast, or they may be painted or coated with materials that comprise contrasting colors, patterns, or textures. Such colors, patterns, or textures may be introduced by any suitable methods, including, but not limited to milling, laser cutting, laser staking, gluing, molding, polymerization, coating, and painting. In some embodiments, multiple patterns or textures may be introduced to either or both of surfaces (602) or (603) using any suitable method, including, but not limited to, stamping, drawing, printing, engraving, scribing, and the like. In some embodiments, the intraocular lens may have two contrasting colors, patterns, or textures, or multiply contrasting colors, patterns, or textures, such as two, or three, or more colors, patterns, or textures.

Figure 7A:
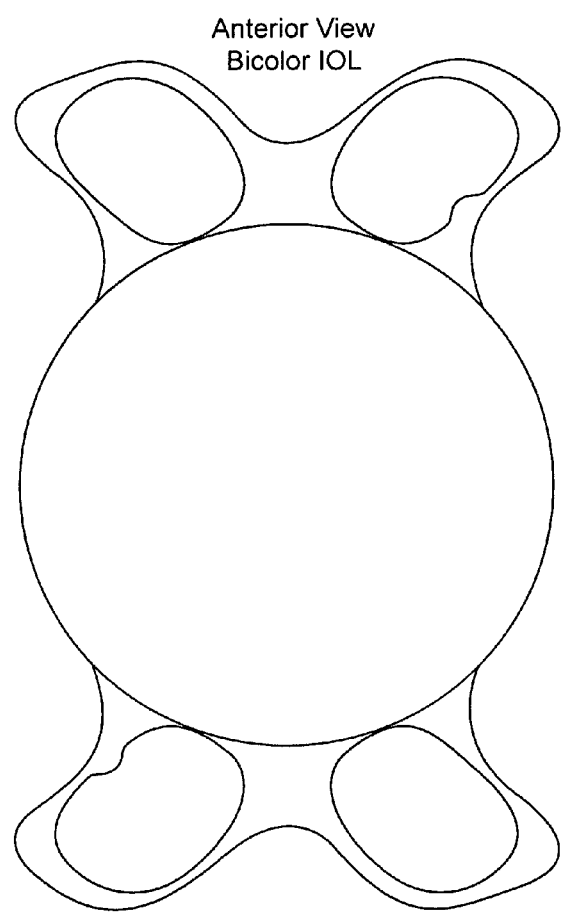
FIG. 7A depicts an anterior view of an intraocular lens.
Figure 7B:
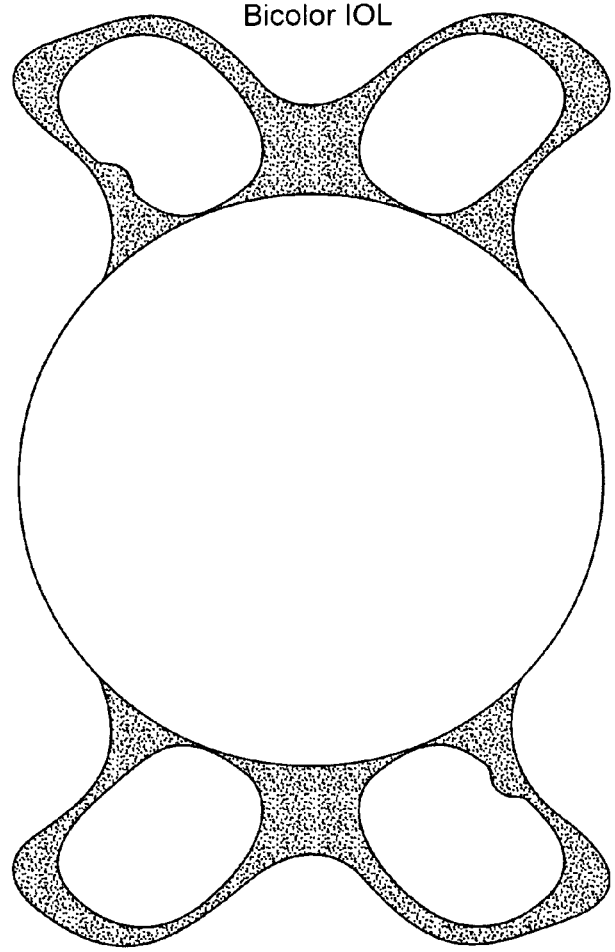
FIG. 7B depicts a posterior view of an intraocular lens.

FIGS. 7A and 7B depict another example of an intraocular lens. In FIG. 7A, the anterior view of the haptics is opaque white in color. In FIG. 7B, the posterior view of the haptics is violet blue in color. Note that the opacity of the haptics prevents the violet blue color from being seen from the anterior side, but allows the violet blue color to be clearly seen from the posterior side.

WORKING EXAMPLES

Example 1

A clear lens blank with a diameter of 12.7 mm and a thickness of 3.00 mm was placed in a cryo-lathe and a ring space was milled around the optic (diameter of 6.00 mm) to a depth of 2.50 mm. 75 mL of 2-hydroxyethyl methacrylate (HEMA), 25 mL methyl methacrylate (MMA), and sufficient ethylene glycol dimethacrylate (EGDMA) to provide a 1.5 wt % loading were mixed together in a propeller mixer for 30 minutes. Sufficient amounts of IRGACURE® 2959 (Ciba/BASF) and IRGACURE® 819 (Ciba/BASF) photoinitiators were added to the mixture to provide 1 wt % loadings of each. The mixture was mixed for 30 minutes. Sufficient copper phthalocyanine, CAS Reg. No. 147-14-8, was added to the mixture to provide a 0.45 wt % loading and then stirred with a propeller mixer for 10 minutes. Sufficient titanium dioxide (R-102 by DuPont) was added to the mixture to provide a 1 wt % loading and the mixture was stirred for an additional 10 minutes.

The mixture was then processed using a Microfluidics Corp. high-shear fluid processing machine (Model 110-EH with a G10Z (87 micron) interaction chamber) at 30,000 psi for 15 cycles. The processed mixture was then poured into a previously milled ring space of a clear lens blank. The filled lens blank was then placed beneath a medium pressure mercury lamp, 11 inches in length and rated at 300 watts/inch (JeLight Inc., Irvine, Calif.). An infra-red mirror was positioned 2 inches beneath the lamp and 5 inches above the substrate. The filled lens blank was exposed to ultraviolet radiation for 2-3 minutes.

The disc was then placed in a cryo-lathe and the blue ringed area was milled to create a ring space with a depth corresponding approximately to the mid-point of the haptic. The shape of the ring space had a positive angulation, meaning that the position of the inner-most region closest to the central optic was posterior to the position of the outer-most region along the "Z" axis.

Next, a mixture of 70 mL HEMA, 25 mL MMA, and a sufficient amount of EGDMA to provide a 1.5 wt % loading were combined and mixed with a propeller mixer for 30 minutes. Sufficient amounts of IRGACURE® 819 (Ciba/BASF) and IRGACURE® 2959 (Ciba/BASF) initiators were added to the mixture to provide 1 wt % loadings of each and the mixture was stirred for 30 minutes. Sufficient titanium dioxide (R-102) to provide an 8 wt % loading was added and stirred for 30 minutes.

The mixture was then processed with a Microfluidics Corp high shear fluid processor (Model 110EH with a G10Z (87 micron) interaction chamber) at 30,000 psi for 15 cycles. The processed mixture was poured into the annular ring space that had previously been milled. The filled lens blank was then placed beneath a medium pressure mercury lamp 11 inches in length, rated at 300 watts/inch (JeLight Inc., Irvine, Calif.). An infra-red mirror was positioned 2 inches beneath the lamp and 5 inches above the substrate. The filled lens blank was exposed to ultraviolet radiation for 2-3 minutes.

What is claimed is:

1. An intraocular lens comprising:
    a central lens optic; and
    at least one haptic projecting outwardly from the central lens optic, said haptic having an anterior side and a posterior side,
    wherein at least one of said anterior and posterior sides of said haptic comprises an opaque first layer that is visually distinct from the other side,
    and further wherein said first layer comprises greater than 1 wt % titanium dioxide.

2. The intraocular lens according to claim 1, wherein said first layer comprises at least about 2 wt % titanium dioxide.

3. The intraocular lens according to claim 1, wherein said first layer comprises one or more of copper phthalocyanine, violet dye, or green dye.

4. The intraocular lens according to claim 1, wherein said first layer comprises at least one polyimide or copolyimide.

5. The intraocular lens according to claim 1, wherein said haptic further comprises at least one second layer having a color that contrasts said first layer and said second layer.

6. The intraocular lens according to claim 5, wherein said second layer comprises one or more of copper phthalocyanine, violet dye, or green dye.

7. The intraocular lens according to claim 5, wherein said second layer comprises at least one polyimide or copolyimide.

8. The intraocular lens according to claim 5, wherein said second layer comprises carbon black.

9. The intraocular lens according to claim 5, wherein the haptic is angulated.

10. A method of using the intraocular lens according to claim 1, the method comprising:
    detecting a visual distinction between said anterior and posterior sides of said haptic of the intraocular lens;
    identifying the lens' orientation from the visual distinction; and
    correcting the lens' orientation if it is different from a predetermined orientation.

11. An intraocular lens comprising a colorless transparent lens optic and at least one haptic projecting outwardly from said lens optic, said haptic having an anterior and an posterior side each comprising a layer, wherein one of said layers is opaque, contains greater than 1% wt titanium dioxide and is visually distinct from the other layer.

12. The intraocular lens of claim 11, wherein each layer is oriented in a plane but spatially separated from each other perpendicular to said plane.

13. The intraocular lens of claim 1, wherein said visual distinction is imparted by using a color, pattern, or texture.

14. The intraocular lens of claim 11, wherein said visual distinction is imparted by using a color, pattern, or texture.

* * * * *